| United States Patent [19] | [11] Patent Number: 4,783,553 |
|---|---|
| Nierth et al. | [45] Date of Patent: Nov. 8, 1988 |

[54] PROCESS FOR ISOLATING DIARYLGUANIDINES

[75] Inventors: Alfred Nierth, Dormagen; Hans Müller, Leverkusen, both of Fed. Rep. of Germany

[73] Assignee: Bayer Aktiengesellschaft, Leverkusen, Fed. Rep. of Germany

[21] Appl. No.: 26,297

[22] Filed: Mar. 16, 1987

[30] Foreign Application Priority Data

Mar. 29, 1986 [DE] Fed. Rep. of Germany ....... 3610594

[51] Int. Cl.$^4$ .......................................... C07C 128/00
[52] U.S. Cl. ..................................... 564/232; 564/238
[58] Field of Search ............................... 564/232, 238

[56] References Cited

U.S. PATENT DOCUMENTS

| 1,727,093 | 9/1929 | Barsky | 564/232 |
| 1,884,509 | 10/1932 | Bailey et al. | 564/232 |
| 1,897,220 | 2/1933 | Horst et al. | 562/232 |

FOREIGN PATENT DOCUMENTS 1518818  2/1976  Fed. Rep. of Germany ...... 564/232

OTHER PUBLICATIONS

Chemical Abstracts, vol. 95, No. 9, Aug. 31, 1981, p. 735, rechte Spalte, Zusammenfassungsnr. 80430q, Columbus, Ohio, U.S.; J. Legocki et al.: "Studies of Diphenylguanidine Production by Reaction of Cyanogen Chloride with Aniline".

*Primary Examiner*—James H. Reamer
*Attorney, Agent, or Firm*—Connolly and Hutz

[57] ABSTRACT

Diarylguanidines can be isolated from the crude melt from the reaction of arylamines and cyanogen chloride in excellent quality and yield by dissolving the hot melt in water, extracting this solution with at least one polar, water-insoluble, organic compound, and precipitating from the purified aqueous solution the diarylguanidine by adding alkali metal hydroxide.

4 Claims, No Drawings

PROCESS FOR ISOLATING DIARYLGUANIDINES

The invention relates to a process for isolating diarylguanidines of high purity in high yield.

In the industrial manufacture of diarylguanidines from anilines, toluidines or xylidines and cyanogen chloride, the reaction product is obtained in the form of a dark melt which consists of the hydrochloride of the corresponding diarylguanidine and undesirable by-products which interfere with the further processing to the pure diarylguanidine (DE-AS (German Published Specification) No. 1,518,818).

The melt has hitherto been purified by dissolving in water and precipitating from the acid diarylguanidine hydrochloride solution the free diarylguanidine by adding alkali metal hydroxide solution.

The diarylguanidine thus isolated, however, is coloured and tends to smudge, since residues of unconverted amine and the by-products formed in the course of the synthesis are coprecipitated.

For further purification, the diarylguanidine hydrochloride solution is treated with active carbon and filtered after an appropriate exposure time (U.S. Pat. No. 1,727,060). Such a process, although effective, is uneconomical.

On the other hand it is known (U.S. Pat. No. 1,897,220; U.S. Pat. No. 1,884,509) to treat the aqueous solution of the diarylguanidines with water-insoluble, apolar hydrocarbons, so that some of the hydrophobic constituents of the impurities can be removed. However, it is not possible to remove all the aminic impurities which, in a diarylguanidine hydrochloride solution, are likewise present as hydrochlorides and which are insoluble in apolar solvents.

It has now been found that diarylguanidines of high purity and with high yields are obtained from crude diarylguanidine hydrochloride melts when the hot melt is dissolved in water, this solution is extracted with at least one polar, water-insoluble organic compound, and from the purified aqueous solution the pure diarylguanidines are precipitated by adding alkali metal hydroxide.

Suitable water-insoluble polar solvents are in particular aliphatic, cycloaliphatic and aromatic chlorohydrocarbons which boil between 80° and 200° C. Preference is given to using chlorobenzene, o-dichlorobenzene and trichlorobenzene.

According to the invention, it is also possible to use mixtures of water-insoluble polar solvents.

A further advantage of the process according to the invention is that, by changing the pH value of the guanidine solution, the process can be adapted to the purification requirements of the guanidine hydrochloride crude solution. For instance, given constant mass flows in the extraction apparatus, uniformly pure diarylguanidine can be produced despite fluctuations in the quality of the crude solution purely by varying the pH value.

The process can be carried out batchwise or continuously. Preference is given to a continuous operation where the solvent mixture is likewise continuously purified from the extracted by-products and returned into the process.

The process is preferably carried out at 20° to 90° C. and pH 5.0 to 7.0.

The weight ratio of crude melt to water is preferably 1:3 to 1:20, very particularly preferably 1:4 to 1:10.

The weight ratio of organic solvent to water is preferably 1:5 to 1:20, very particularly preferably 1:7 to 1:14.

EXAMPLE 1

(a) 50 g of a warm diphenylguanidine hydrochloride crude melt at about 160° C. from the reaction of aniline and cyanogen chloride (DE-AS (German Published Specification) No. 1,518,818) were stirred into 280 g of hot water. A brown aqueous solution formed, although undissolved matter was still present.

This solution was cooled with stirring to 60° C., and 15 g of 1,2,4-trichlorobenzene were added.

After a pH value of 6.6 had been set with sodium hydroxide solution, the stirrer was switched off.

The phases separated at once. The aqueous phase was separated off and extracted once more with 15 g of 1,2,4-trichlorobenzene at pH 6.6.

Then the sodium hydroxide solution was added to pH 11.8 to precipitate colourless diphenylguanidine. It was washed with water and dried. The yield was 93.5% of theory.

Titrimetric analysis gave a content of 98.6% and a melting point of 149.4° C.

(b) For comparison, 50 g of the same crude melt were dissolved in 280 g of hot water. By adding sodium hydroxide solution the diphenylguanidine was precipitated from the solution of pH 11.8.

The result was a beige-coloured product, which was washed with water and dried. The yield was 98.3% of theory.

Active substance content (titrimetric): 98.1%
Melting range: 143.1°-145.4° C.
Colour: beige.

EXAMPLE 2

(a) 50 g of the warm crude melt were dissolved in 280 g of hot water. The aqueous solution was cooled down and extracted twice with 15 g of o-dichlorobenzene.

The pH was brought to 6.9 with sodium hydroxide solution. After separation of the phases the diphenylguanidine was precipitated by adding sodium hydroxide solution.

The product was colourless and has a melting point of 146.8° C. The yield was 94.1% of theory.

EXAMPLE 3

(a) In a trial operated on a continous basis, 30 L/h of an approximately 30% strength by weight aqueous crude diphenylguanidine hydrochloride solution were diluted to 15% by weight by adding water and thermostated in a buffer vessel to 60° C. The aqueous solution was then continuously extracted in countercurrent with 2 L/h of 1,2,4-trichlorobenzene.

The pH was brought to 6.9 by simultaneously adding sodium hydroxide solution.

The trial was carried out in a 4-stage mixer-separator battery.

The aqueous solution flowing out of the unit was analytically investigated at regular intervals.

Melting point: 147.5° C.
Active substance content (titrimetric): 98.5%
The yield was 93.2% of theory.

(b) In parallel therewith, a sample was taken from the crude diphenylguanidine hydrochloride solution, and the quality thereof was determined by isolating the product by stirring into sodium hydroxide solution until pH 11.8. The melting range was 141.1°-144.3° C.; the colour of the product was yellow. The yield was 98.1% of theory.

We claim:

1. Process for isolating diarylguanidines from the crude melt obtained from reacting arylamines and cyanogenchloride, characterized in that the hot melt is dissolved in water and the resulting solution is extracted with aliphatic, cycloaliphatic or aromatic chlorohydrocarbons having a boiling point between 80° and 200° C. at a temperature between 20° C. and 90° C. and within a pH range of 5.0 to 7.0, and then precipitating diarylguanidine from the extraction-purified aqueous solution by mixing the solution with alkali metal hydroxide.

2. In the process for isolating diarylguanidines from the crude melt obtained from reacting arylamines and cyanogenchloride, the improvement comprises:
   (i) dissolving the hot melt in water at a weight ratio of melt:water of from 1:3 to 1:20 to form an aqueous solution,
   (ii) extracting the solution with aliphatic, cycloaliphatic or aromatic chlorohydrocarbons having a boiling point between 80° and 200° C. at a temperature between 20° C. and 90° C. and within a pH range of 5.0 to 7.0, with the weight ratio of chlorohydrocarbons : water of from 1:5 to 1:20, and then separating the aqueous solution from the chlorohydrocarbon extract, and
   (iii) precipitating diarylguanidine from the extraction-purified aqueous solution by mixing the solution with alkali metal hydroxide.

3. Process according to claim 1, characterized in that the weight ratio of cruce melt:water is 1:3 to 1:20.

4. Process according to claim 1, characterized in that the weight ratio of chlorohydrocarbon:water is 1:5 to 1:20.

* * * * *